US011112143B2

(12) United States Patent
Yokoyama et al.

(10) Patent No.: US 11,112,143 B2
(45) Date of Patent: Sep. 7, 2021

(54) FAN FILTER UNIT, STERILIZATION APPARATUS AND CLEAN ROOM

(71) Applicant: Hitachi Industrial Equipment Systems Co., Ltd., Tokyo (JP)

(72) Inventors: Makoto Yokoyama, Tokyo (JP); Takeshi Matsumura, Tokyo (JP); Hirotoshi Sato, Tokyo (JP)

(73) Assignee: Hitachi Industrial Equipment Systems Co., Ltd., Tokyo (JP)

( * ) Notice: Subject to any disclaimer, the term of this patent is extended or adjusted under 35 U.S.C. 154(b) by 169 days.

(21) Appl. No.: 16/470,276

(22) PCT Filed: Feb. 15, 2018

(86) PCT No.: PCT/JP2018/005258
§ 371 (c)(1),
(2) Date: Jun. 17, 2019

(87) PCT Pub. No.: WO2018/225298
PCT Pub. Date: Dec. 13, 2018

(65) Prior Publication Data
US 2020/0096229 A1   Mar. 26, 2020

(30) Foreign Application Priority Data

Jun. 6, 2017   (JP) .............................. JP2017-111702

(51) Int. Cl.
*F24F 13/28*   (2006.01)
*B01L 1/00*   (2006.01)
(Continued)

(52) U.S. Cl.
CPC ............... *F24F 13/28* (2013.01); *B01L 1/00* (2013.01); *F24F 7/06* (2013.01); *F24F 3/167* (2021.01);
(Continued)

(58) Field of Classification Search
CPC .... A61L 9/015; F24F 3/16; F24F 7/06; B08B 15/023; B08B 15/02; B08B 15/026; F24C 13/28; B01L 1/00
(Continued)

(56) References Cited

U.S. PATENT DOCUMENTS 3,505,989 A * 4/1970 Andrew ............... A61G 10/005
600/21
4,952,283 A * 8/1990 Besik ..................... F24F 3/1411
165/4
(Continued)

FOREIGN PATENT DOCUMENTS

| EP | 0 847 760 A2 | 6/1998 |
| JP | 63-291616 A | 11/1988 |

(Continued)

OTHER PUBLICATIONS

International Search Report (PCT/ISA/210) issued in PCT Application No. PCT/JP2018/005258 dated Apr. 3, 2018 with English translation (five pages).

(Continued)

Primary Examiner — Vivek K Shirsat
(74) Attorney, Agent, or Firm — Crowell & Moring LLP

(57) ABSTRACT

Provided are a fan filter unit and a sterilization apparatus capable of shortening a sterilization operation time to be performed at a changeover. The sterilization apparatus has: a working space; a fan filter unit for supplying clean air to the working space; and a sterilizing gas charging unit on the air suction side of the fan filter unit. The fan filter unit comprises: a fan unit section constituted by an air blower and a pressurization chamber; a dust removal filter provided on the downstream side of the fan unit section; a passage bypassing the dust removal filter; and an opening and closing mechanism of the passage. By opening the opening and closing mechanism, the air flow not passing through the (Continued)

dust removal filter can be supplied to the secondary side of the fan filter unit.

10 Claims, 6 Drawing Sheets

(51) Int. Cl.
| | | |
|---|---|---|
| *F24F 7/06* | (2006.01) | |
| *F24F 7/007* | (2006.01) | |
| *F24F 13/20* | (2006.01) | |
| *F24F 3/167* | (2021.01) | |
| *F24F 8/108* | (2021.01) | |

(52) U.S. Cl.
CPC ............... *F24F 7/007* (2013.01); *F24F 8/108* (2021.01); *F24F 13/20* (2013.01)

(58) Field of Classification Search
USPC .............................................. 454/187, 56–62
See application file for complete search history.

(56) References Cited

U.S. PATENT DOCUMENTS

| | | | |
|---|---|---|---|
| 5,501,844 A | * | 3/1996 | Kasting, Jr. .............. A61L 9/015 422/186.15 |
| 2004/0262241 A1 | * | 12/2004 | Socha ..................... A61L 9/015 210/760 |
| 2005/0084431 A1 | | 4/2005 | Hill et al. |
| 2017/0082305 A1 | * | 3/2017 | Law ................... B01D 46/0036 |

FOREIGN PATENT DOCUMENTS

| | | |
|---|---|---|
| JP | 64-5033 U | 1/1989 |
| JP | 3-175224 A | 7/1991 |
| JP | 10-272176 A | 10/1998 |
| JP | 2000-316962 A | 11/2000 |
| JP | 2006-271583 A | 10/2006 |
| JP | 2007-505715 A | 3/2007 |
| JP | 2011-167405 A | 9/2011 |

OTHER PUBLICATIONS

Japanese-language Written Opinion (PCT/ISA/237) issued in PCT Application No. PCT/JP2018/005258 dated Apr. 3, 2018 (five pages).

* cited by examiner

FAN FILTER UNIT, STERILIZATION APPARATUS AND CLEAN ROOM

TECHNICAL FIELD

The present invention relates to a fan filter unit in which an air blower and a filter are combined to supply clean air, and a sterilization apparatus and a clean room using the same.

BACKGROUND ART

In a regenerative medicine which repairs or replaces lost functions, or in a cell therapy which treats or alleviates diseases or injuries by administering cells, as a manufacturing environment in a culture pretreatment process using cells or tissues (hereinafter referred to as "samples") extracted from patients, it is necessary to manufacture in a working space with a certain degree of cleanliness, reduce the risk of contamination to the sample, prevent the diffusion of the sample into a working chamber, and prevent mutual contamination between different samples. Therefore, a safety cabinet or an isolator system is used, and a clean booth is used as a culture environment of the sample.

A fan filter unit which supplies clean air to a sterilization space is mounted on a sterilization apparatus such as a safety cabinet, an isolator system and a clean booth.

In order to improve an operation rate of manufacturing facilities, important areas or culture devices are shared for sample processed products from a plurality of patients in a processing course in the same period, and after a processing step, for example, using a certain patient's sample is completed, when switching to a processing step using samples of different patients (hereinafter referred to as "changeover"), it is necessary to sterilize a manufacturing device including a sterilization apparatus.

Patent Document 1 discloses an example of a sterilization treatment method of an isolator, and discloses that "the sterilizing gas is supplied to the inside of the working space, while causing the gas in the working space of the isolator to circulate via a circulating filter, using a first circulation flow path, thereby performing the sterilization treatment of the working space, and after a predetermined time elapses, the supply of the sterilizing gas is stopped, and the first circulation flow path is switched to a second circulation flow path to cause the gas to pass through a detoxifying device disposed in the second circulation flow path, thereby detoxifying the sterilizing gas contained in the circulating gas and setting the working space of the isolator to an sterilization environment at a high level" (Abstract).

CITATION LIST

Patent Document

Patent Document 1: JP 2011-167405 A

SUMMARY OF THE INVENTION

Problems to be Solved by the Invention

In order to improve the operation rate of the production facilities, it is important to reduce the time required for the sterilizing work that occurs at each changeover. The sterilizing work is to fill the sterilizing gas to a concentration that allows sterilization inside the sterilization apparatus and expose the sterilizing gas for a certain period of time to kill or eliminate microorganisms.

FIG. 4 illustrates an example of a fan filter unit and a sterilization apparatus of related art. A sterilization apparatus 100 includes a working space 1, a fan filter unit 2 which supplies normal air to the working space, and a sterilizing gas charging port 8 on a primary side of the fan filter unit. The fan filter unit 2 is configured to include a fan unit section including an air blower 3 and a pressurization chamber 4, and a dust removal filter 5 provided on a downstream side of the fan unit section.

In the process of the sterilizing work of related art, first, in order to fill the sterilizing gas into the sterilization apparatus, an opening which disturbs the filling of the sterilizing gas in the sterilization apparatus is blocked. Next, from the sterilizing gas charging port 8 disposed on the primary side of the dust removal filter 5 of the fan filter unit 2 for supplying the clean air to the working space 1 in the sterilization apparatus, the sterilizing gas is charged until reaching a concentration which makes the primary side of the dust removal filter 5 of the fan filter unit and the sterilization space that performs the cell processing work on the secondary side of the dust removal filter 5 sterilizable.

Further, the sterilization is completed by maintaining the condition within the prescribed sterilization time, while maintaining the primary side of the dust removal filter 5 and the sterilization space at a prescribed concentration for sterilizing. After completion of sterilization, in order to reduce the concentration of sterilizing gas on the primary side of the dust removal filter 5 and the sterilization space to a level that does not affect the next cell processing work, in a state where a place in which the sterilization apparatus is closed for filling the charging of the sterilizing gas is opened and the charging of the sterilizing gas is stopped, the fan filter unit 2 is operated for a certain period of time to remove the remaining sterilizing gas.

In the above-mentioned sterilizing work flow, it takes the most time for the process of setting the sterilizing gas of the primary side of the dust removal filter and the sterilization space to a prescribed concentration.

In order to shorten the working time of the sterilizing work, it is necessary to make the concentration of the sterilizing gas of the primary side of the dust removal filter and the sterilization space to a prescribed concentration in a short time. However, when the concentration of sterilizing gas charged is increased from the sterilizing gas charging port on the primary side of the dust removal filter, the sterilizing gas is more likely to liquefy (particulate) due to a change in dew point, and if the sterilizing gas liquefies, there is also a problem that the sterilizing gas is collected by the dust removal filter and a supply amount of sterilizing gas supplied to the secondary side of the dust removal filter decreases.

In related art, as a method of shortening the time required for sterilization, as illustrated in FIG. 4, a sterilizing gas charging port 9 is also additionally provided in the sterilization space on the secondary side of the dust removal filter, and the sterilizing gas is charged from the sterilizing gas charging ports of two systems, thereby trying to shorten the sterilizing gas filling time of the primary side of the dust removal filter and the sterilization space. However, by additionally disposing the sterilizing gas charging port in the sterilization space of the secondary side of the dust removal filter, the cost of the sterilizing gas charging facility and the preparation time at the time of sterilizing gas charging are generated, and there is a problem that improves this.

An object of the invention is to provide a fan filter unit and a sterilization apparatus capable of shortening the sterilization operation time to be performed at the time of a changeover.

Solutions to Problems

According to an example of the invention for achieving the above object, there is provided a fan filter unit including a fan unit section constituted by an air blower and a pressurization chamber, and a dust removal filter provided on a downstream side of the fan unit section, in which a passage bypassing the dust removal filter and an opening and closing mechanism of the passage are provided, and by opening the opening and closing mechanism, an air flow not passing through the dust removal filter can be supplied to a secondary side of the fan filter unit.

In addition, according to an example of the invention, there is provided a sterilization apparatus having a working space, a fan filter unit configured to supply clean air to the working space, and a sterilizing gas charging unit on a suction side of air of the fan filter unit, in which the fan filter unit includes: a fan unit section constituted by an air blower and a pressurization chamber; a dust removal filter provided on a downstream side of the fan unit section; a passage bypassing the dust removal filter; and an opening and closing mechanism of the passage, and by opening the opening and closing mechanism, an air flow not passing through the dust removal filter can be supplied to a secondary side of the fan filter unit.

Effects of the Invention

According to the fan filter unit and the sterilization apparatus according to the invention, it is possible to shorten the time of sterilizing work performed at the time of changeover.

MODE FOR CARRYING OUT THE INVENTION

Figure 1:
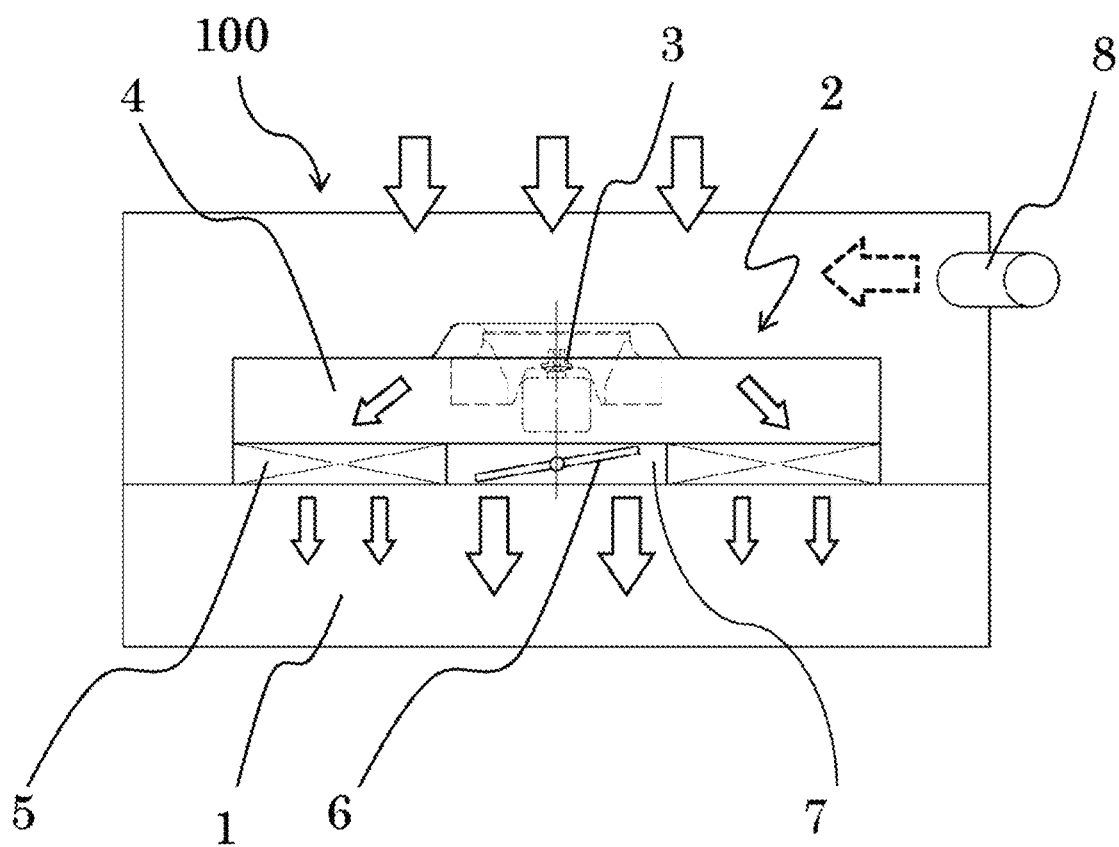
FIG. 1 is a schematic view of a fan filter unit and a sterilization apparatus of Example 1 of the invention.

Hereinafter, embodiments of the invention will be described on the basis of the drawings. In each drawing illustrating the embodiments, the same constituent elements are denoted by the same names and reference numerals as much as possible, and the repetitive description thereof will not be provided.

Example 1

FIG. 1 is a schematic view of the inside of a sterilization apparatus illustrating Example 1 of the invention.

A sterilization apparatus 100 includes a sterilizing working space 1 (hereinafter referred to as a "working space") for processing cells, and a fan filter unit 2 which supplies clean air to the working space. The fan filter unit 2 includes a fan unit section including an air blower 3 and a pressurization chamber 4, and a dust removal filter 5 such as a HEPA filter disposed downstream of the fan unit section. Furthermore, the fan filter unit 2 includes a passage 7 that diverts the air flow and an opening and closing mechanism 6 that opens and closes the passage 7, for supplying the air flow to the secondary side of the fan filter unit 2 without passing through the dust removal filter 5. In this example, the passage 7 bypassing the dust removal filter 5 is disposed at a position passing through the surface to which the dust removal filter 5 is attached.

Further, as illustrated in the drawing, the passage 7 bypassing the dust removal filter 5 is disposed on a rotation axis of the air blower 3. The passage 7 bypassing the dust removal filter 5 may be disposed on a periphery of the dust removal filter, without being limited to the rotation axis of the air blower 3, or may be provided in plurality instead of one.

In the sterilization apparatus 100, a sterilizing gas charging port 8 used at the time of sterilizing work is disposed on an air charging side of the fan filter unit 2 and the primary side of the dust removal filter 5.

Next, the operation of the fan filter unit 2 of this example will be described. At the time of normal sample processing, external air taken in by the fan filter unit 2 mounted on the sterilization apparatus 100 is filtered by the dust removal filter 5 and the clean air is supplied to the working space 1.

At the time of sterilizing work, the opening and closing mechanism 6 of the passage 7 disposed on the secondary side of the fan unit section of the fan filter unit 2 is opened to provide an opening, while setting the air blower 3 of the fan filter unit in an operation state. The sterilizing gas is supplied to the working space 1 on the secondary side of the fan filter unit, without passing through the dust removal filter 5. However, since the dust removal filter 5 also needs to be sterilized, an opening area of the opening and closing mechanism 6 is set to an area such that the air flow filtered by the dust removal filter 5 can also be supplied to the working space 1 on the secondary side of the fan filter unit.

In this state, the sterilizing gas is charged from the sterilizing gas charging port 8 provided on the primary side of the dust removal filter 5 of the fan filter unit 2 in the sterilization apparatus. The air containing the sterilizing gas is sent to the pressurization chamber 4 by the air blower 3, and at this time, a part of the sterilizing gas is supplied to the cell processing working space on the secondary side of the fan filter unit via the dust removal filter 5, and most of the sterilizing gas is supplied to the working space on the secondary side of the fan filter unit via the passage 7 equipped with the opening and closing mechanism 6. Since most of the sterilizing gas is supplied to the cell processing working space on the secondary side of the fan filter unit 5 via the passage 7 bypassing the dust removal filter 5, the interior of the working space 1 can reach a prescribed concentration at the time of sterilization in a short time.

Thereafter, after the sterilization of the dust removal filter 5 and the working space 1 is completed, since it is necessary to lower the concentration of the sterilizing gas, the charging of the sterilizing gas is stopped and the passage 7 equipped with the opening and closing mechanism 6 is closed, and by continuing to operate the fan filter unit 2, it is possible to recover the cleanliness lowered by the sterilizing gas of the working space 1.

According to this example, it is possible to shorten the sterilization operation time to be performed at the time of changeover.

Also, in related art, in order to increase the concentration of sterilizing gas in the cell processing working space on the downstream side of the fan filter unit, the sterilizing gas charging port is also provided on the downstream side of the fan filter unit. However, since the sterilizing gas charging port becomes unnecessary, it is also reduce the cost and the number of man-hours for preparation thereof.

Further, since the passage bypassing the dust removal filter is disposed at a position passing through the surface to which the dust removal filter is attached, air containing the sterilizing gas can be efficiently sent to the working space. Furthermore, since the passage bypassing the dust removal filter is disposed on the rotation axis of the air blower, the air containing the sterilizing gas can be efficiently sent to the working space more efficiently.

Example 2

Figure 2:
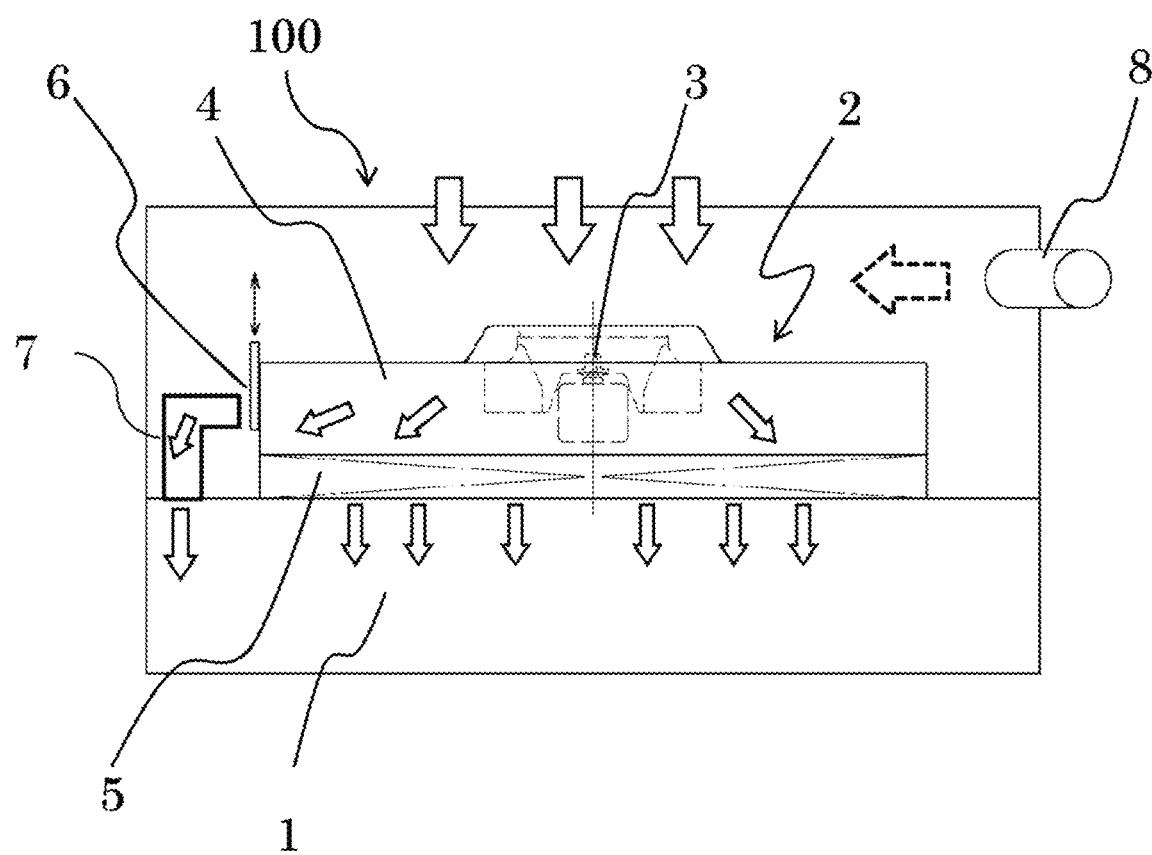
FIG. 2 is a schematic view of a fan filter unit and a sterilization apparatus of Example 2 of the invention.

FIG. 2 is a schematic view of the inside of a sterilization apparatus illustrating Example 2 of the invention.

In the fan filter unit of Example 2, an opening equipped with the opening and closing mechanism 6 is provided on a side surface of the pressurization chamber 4 of the fan unit section. Further, a passage 7 connecting the opening and the working space 1 on the secondary side of the fan filter unit 2 and bypassing the dust removal filter 5 is provided. The bypassing passage 7 may be integrally attached to the fan filter unit 2 on the outer side of the pressurization chamber, or may be disposed separately from the fan filter unit.

According to this example, the opening equipped with the opening and closing mechanism to discharge the air flow, and the passage connecting the opening and the secondary side of the fan filter unit are provided on the side surface of the pressurization chamber. Thus, in addition to the effects of Example 1, the fan filter unit can be manufactured without much changing the structure of the fan filter unit of related art.

Example 3

Figure 3:
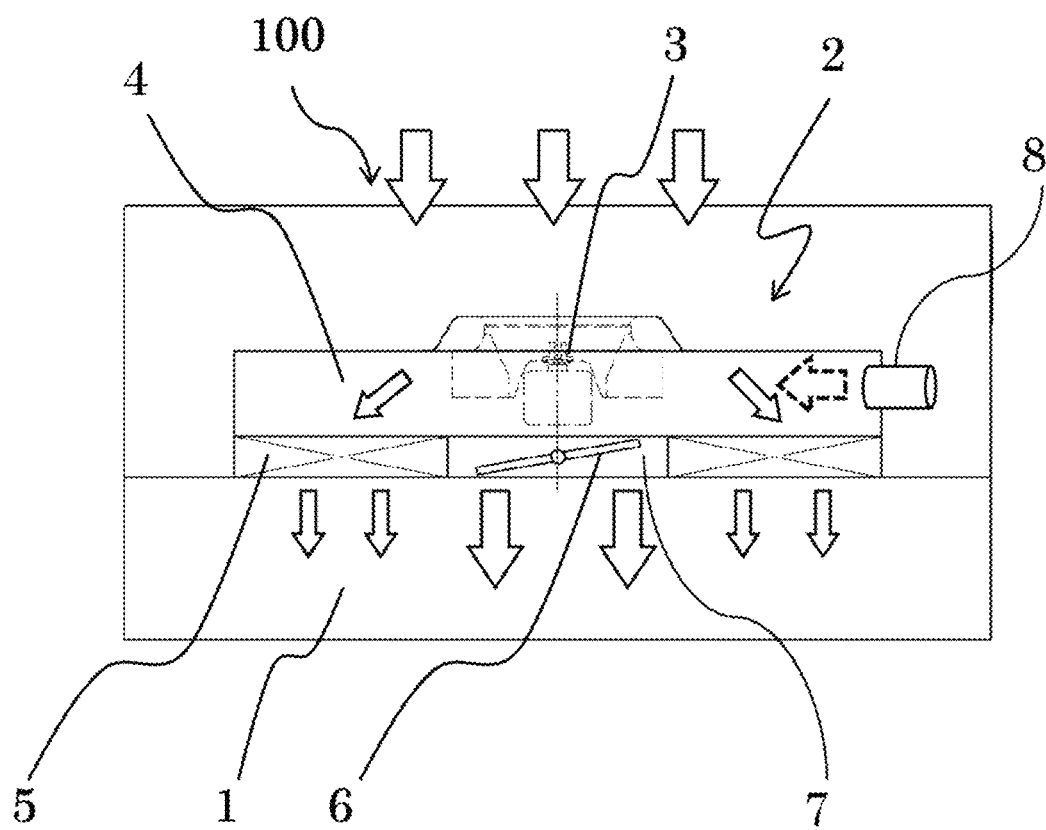
FIG. 3 is a schematic view of a fan filter unit and a sterilization apparatus of Example 3 of the invention.
Figure 4:
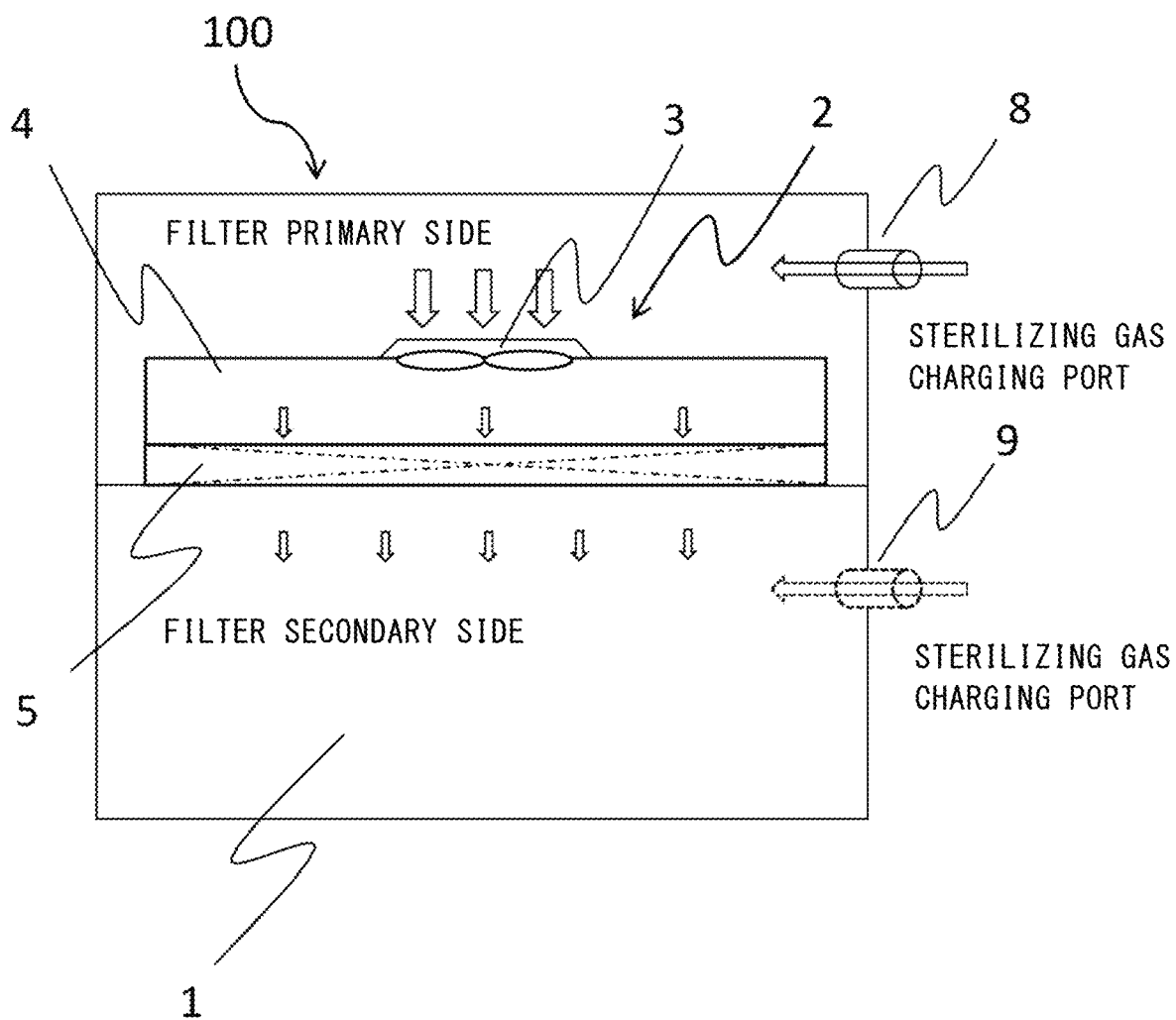
FIG. 4 is a schematic view illustrating an example of a fan filter unit and a sterilization apparatus of related art.

FIG. 3 is a schematic view of the inside of a sterilization apparatus illustrating Example 3 of the invention.

In the sterilization apparatuses of Example 1 and Example 2, the sterilizing gas charging port 8 is provided separately from the fan filter unit 2. However, in Example 3, the sterilizing gas charging port 8 is disposed in the fan filter unit 2. That is, as illustrated in the drawing, the sterilizing gas charging port 8 is provided in the pressurization chamber 4 so that the sterilizing gas can be directly charged into the pressurization chamber 8. Although the sterilizing gas charging port 8 is provided on the side surface of the pressurization chamber in the drawing, the sterilizing gas charging port 8 may be provided on the upper surface of the pressurization chamber, or a plurality of the sterilizing gas charging ports 8 may be provided.

According to this example, since the sterilizing gas charging port is provided in the pressurization chamber so that the sterilizing gas can be directly charged into the pressurization chamber, the sterilizing gas can be efficiently supplied to the working space. In addition, since a sterilizing gas charging means is provided integrally with the fan filter unit, there is no need to separately arrange the sterilizing gas charging means, and only by attaching the fan filter unit of this example to the sterilization apparatus, the sterilization apparatus with a sterilization means can be configured.

Example 4

Figure 5:
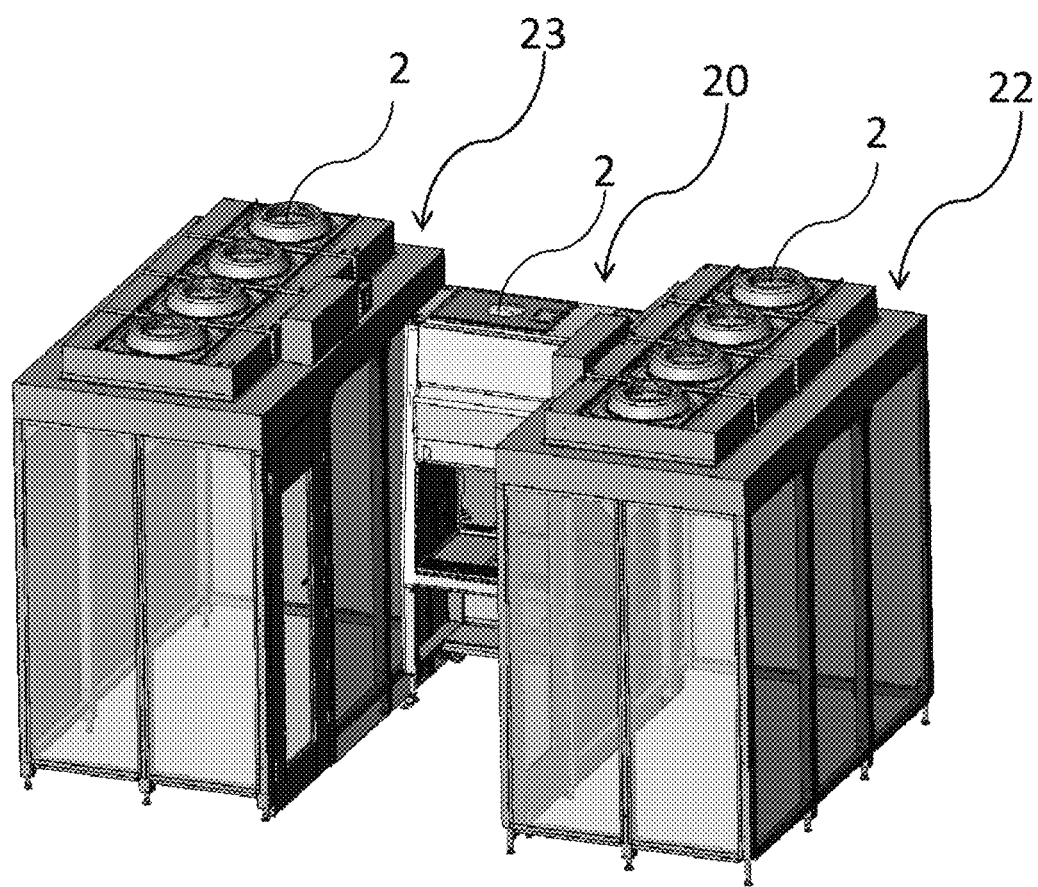
FIG. 5 is a view illustrating an example of a safety cabinet of Example 4 of the invention.

FIG. 5 is a schematic view of a sterilization apparatus illustrating Example 4 of the invention. In this example, the fan filter unit of the invention is used in a safety cabinet and a clean booth.

In the drawing, a safety cabinet 20 is disposed at the center, a clean booth 22 of a reception side for receiving the samples and the like is disposed on a right side of the safety cabinet, and a clean booth 23 of an extraction side for extracting the samples and the like is disposed on a left side of the safety cabinet. Since the fan filter unit 2 of Examples 1 to 3 is attached to the upper side of the safety cabinet 20, the safety cabinet can be sterilized in a short time at the time of sterilization of the working space and the like. Further, since the fan filter unit 2 of Examples 1 to 3 is attached also to the upper surfaces of the clean booth 22 on the reception side and the clean booth 23 on the extraction side, the clean booth can be sterilized in a short time.

In addition, although the safety cabinet is described as a sterilization apparatus which performs the treatment in FIG. 5, an isolator may also be used. Also, a pass box may be used instead of the clean booth.

Example 5

Figure 6:
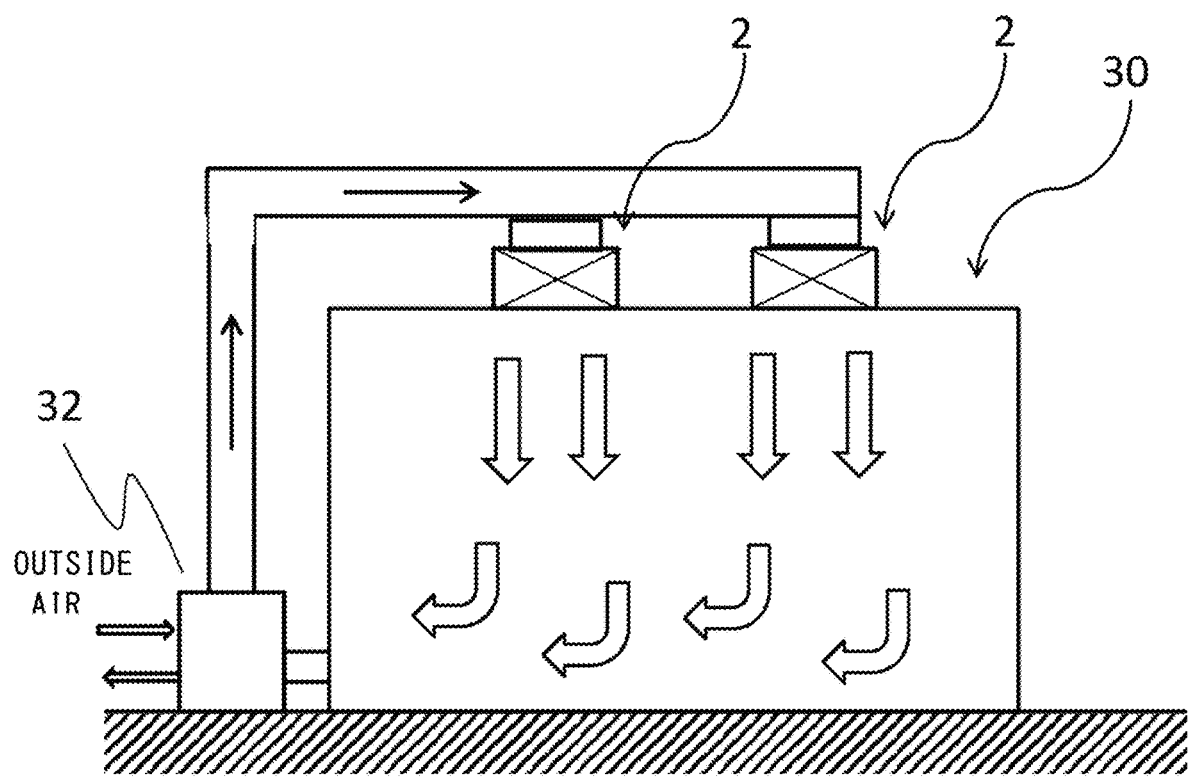
FIG. 6 is a schematic view illustrating an example of a clean room of Example 5 of the invention.

FIG. 6 is a schematic view of a sterilization apparatus illustrating Example 5 of the invention. In this example, the fan filter unit of the invention is used in a clean room.

In the drawing, a plurality of fan filter units 2 is attached to the upper part of the working chamber of a clean room 30. Further, an air conditioner 32 is provided in communication with the lower part of the working chamber, and the air conditioner 32 and the fan filter unit 2 are connected by an air passage. Furthermore, the air conditioner 32 is capable of sucking in and discharging the outside air. At the time of operation of the clean room 30, as indicated by the arrows, the air sent from the air conditioner 32 is supplied as clean air to the working chamber of the clean room through the fan filter unit 2 equipped with the dust removal filter, and returns to the air conditioner 32 from the working chamber to circulate air. This keeps the working chamber of the clean room in a clean state. Further, by attaching the fan filter unit 2 of Examples 1 to 3 as a fan filter unit, it is possible to sterilize the clean room in a short time at the time of sterilization of the working chamber or the like.

INDUSTRIAL APPLICABILITY

The invention can be used to a fan filter unit or the like that supply the clean air to the sterilization space of a sterilization apparatus (a safety cabinet, an isolator, a clean booth) or a clean room used to handle cells, microorganisms and pathogens, for example, in the field of regenerative medicine for culturing cells, and in the industrial fields of medicines and pharmaceuticals for handling of pathogens and genetic manipulation.

REFERENCE SIGNS LIST

1 Working space of sterilization apparatus
2 Fan filter unit
3 Air blower
4 Pressurization chamber 5 Dust removal filter
6 Opening and closing mechanism
7 Air passage
8 Sterilizing gas charging port on primary side of dust removal filter
9 Sterilizing gas charging port on secondary side of dust removal filter
20 Safety cabinet
22 Clean booth (reception side)
23 Clean booth (extraction side)
30 Clean room
32 Air conditioner
100 Sterilization apparatus

The invention claimed is:

1. A fan filter unit including a fan unit section constituted by an air blower and a pressurization chamber, and a dust removal filter provided on a downstream side of the fan unit section, comprising:
a passage bypassing the dust removal filter;
an opening and closing mechanism of the passage; and
an opening equipped with the opening and closing mechanism to discharge the air flow provided on a side surface of the pressurization chamber;
wherein the passage connects the opening and a secondary side of the fan filter unit, and
wherein by opening the opening and closing mechanism, an air flow not passing through the dust removal filter can be supplied to the secondary side of the fan filter unit.

2. The fan filter unit according to claim 1, wherein the passage bypassing the dust removal filter is provided at a position passing through a surface to which the dust removal filter is attached.

3. The fan filter unit according to claim 1, wherein a sterilizing gas charging unit is provided in the pressurization chamber.

4. A sterilization apparatus having a working space, a fan filter unit configured to supply clean air to the working space, and a sterilizing gas charging unit on a suction side of air of the fan filter unit,
wherein the fan filter unit includes:
a fan unit section constituted by an air blower and a pressurization chamber;
a dust removal filter provided on a downstream side of the fan unit section;
a passage bypassing the dust removal filter; and
an opening and closing mechanism of the passage,
wherein by opening the opening and closing mechanism, an air flow not passing through the dust removal filter can be supplied to a secondary side of the fan filter unit;
wherein an opening equipped with the opening and closing mechanism to discharge the air flow is provided on a side surface of the pressurization chamber of the fan filter unit, and
wherein the passage connects the opening and the working space.

5. The sterilization apparatus according to claim 4, wherein the passage bypassing the dust removal filter is provided at a position passing through a surface to which the dust removal filter of the fan filter unit is attached.

6. The sterilization apparatus according to claim 4, wherein the sterilization apparatus is a clean booth.

7. The sterilization apparatus according to claim 4, wherein the sterilization apparatus is a safety cabinet.

8. The sterilization apparatus according to claim 4, wherein the sterilization apparatus is an isolator.

9. The sterilization apparatus according to claim 4, wherein the sterilization apparatus is a clean room.

10. A clean room having an air blowing path equipped with an air blower and a sterilization apparatus, and a working chamber to which air is blown via the sterilization apparatus connected to the air blowing path, the clean room comprising:
a freely openable and closable opening and closing unit; and
a second air blowing path connected to a sterilizing gas insertion unit, passing through the opening and closing unit opened from the air blower without passing through the sterilization apparatus and connected to the working chamber;
wherein the sterilization apparatus has a fan filter unit configured to supply clean air to the working chamber, and a sterilizing gas charging unit on a suction side of air of the fan filter unit;
wherein the fan filter unit includes:
a fan unit section including the air blower and a pressurization chamber;
a dust removal filter provided on a downstream side of the fan unit section;
a passage bypassing the dust removal filter; and
an opening and closing mechanism of the passage,
wherein by opening the opening and closing mechanism, an air flow not passing through the dust removal filter can be supplied to a secondary side of the fan filter unit,
wherein an opening equipped with the opening and closing mechanism to discharge the air flow is provided on a side surface of the pressurization chamber of the fan filter unit, and
wherein the passage connects the opening and the working chamber.

* * * * *